US008403959B2

(12) United States Patent
Döllinger (10) Patent No.: US 8,403,959 B2
(45) Date of Patent: Mar. 26, 2013

(54) IMPLANT FOR THE TREATMENT OF LUMBAR SPINAL CANAL STENOSIS

(75) Inventor: Horst Döllinger, Schillingsfürst (DE)

(73) Assignee: Med-Titan Spine GmbH, Erlangen (DE)

( * ) Notice: Subject to any disclaimer, the term of this patent is extended or adjusted under 35 U.S.C. 154(b) by 977 days.

(21) Appl. No.: 11/721,801

(22) PCT Filed: Dec. 16, 2005

(86) PCT No.: PCT/IB2005/003799
§ 371 (c)(1),
(2), (4) Date: Jun. 14, 2007

(87) PCT Pub. No.: WO2006/064356
PCT Pub. Date: Jun. 22, 2006

(65) Prior Publication Data
US 2009/0254185 A1 Oct. 8, 2009

(30) Foreign Application Priority Data

Dec. 16, 2004 (CH) .................................. 2084/04
Aug. 16, 2005 (CH) .................................. 1344/05

(51) Int. Cl.
*A61B 17/70* (2006.01)
(52) U.S. Cl. ............... 606/249; 606/248; 623/17.11
(58) Field of Classification Search ............ 606/53, 606/60, 90, 246, 248, 249, 257, 263, 304, 606/310, 313, 314, 319; 623/17.11–17.16
See application file for complete search history.

(56) References Cited

U.S. PATENT DOCUMENTS

| 2,077,804 | A | * | 4/1937 | Morrison | 606/68 |
|---|---|---|---|---|---|
| 3,168,850 | A | * | 2/1965 | Tennican | 411/342 |
| 4,721,103 | A | * | 1/1988 | Freedland | 606/319 |
| 5,098,433 | A | * | 3/1992 | Freedland | 606/63 |
| 6,027,504 | A | * | 2/2000 | McGuire | 606/87 |
| 6,482,210 | B1 | * | 11/2002 | Skiba et al. | 606/86 R |
| 2002/0183746 | A1 | * | 12/2002 | Zucherman et al. | 606/61 |
| 2005/0245937 | A1 | * | 11/2005 | Winslow | 606/90 |

FOREIGN PATENT DOCUMENTS

| WO | 99/21501 A1 | 5/1999 |
|---|---|---|
| WO | 01/95818 A1 | 12/2001 |
| WO | 03/057054 A2 | 7/2003 |
| WO | WO 2004100840 A1 * | 11/2004 |
| WO | 2005/009300 A1 | 2/2005 |

* cited by examiner

*Primary Examiner* — Eduardo C Robert
*Assistant Examiner* — Lynnsy Schneider
(74) *Attorney, Agent, or Firm* — Speckman Law Group PLLC; Janet Sleath (57) ABSTRACT

Disclosed is an implant for treating lumbar spinal canal stenosis, comprising a spacer that is proved with an elongate interior space into which an insert part can be inserted. A first retaining element is fixed in the spacer in the inserted state. Said first retaining part can be folded apart by inserting the insert part while a second rear retaining element that is molded onto the insert part simultaneously comes to rest on the vertebral processes, thus making it possible to insert the implant unilaterally while reducing the risk of having to undergo possible postoperative interventions.

10 Claims, 12 Drawing Sheets

IMPLANT FOR THE TREATMENT OF LUMBAR SPINAL CANAL STENOSIS

FIELD OF THE INVENTION

The present invention relates to an implant for treating lumbar spinal canal stenosis, with a spacer which may be attached between spinous processes of two adjacent vertebral bodies.

BACKGROUND OF THE INVENTION

Spinal canal stenosis is to be understood as any form of narrowing of the spinal canal through which the spinal chord runs, whilst excluding inflammation, tumors and complete slipped disks. Most commonly, spinal canal stenosis takes place in the region of the lumbar spine, but it also occurs in the region of the thoracic spine and cervical spine. The most common cause of the acquired spinal canal stenosis is degenerative changes on the spinal column. Such degenerative changes of the bone-cartilage system occur more commonly with older patients. Therapeutically, one initially intervenes with anesthetic medication, such as non-steroid anti-rheumatics or by way of creating a lordosis correction by way of bandages or corsets. If this is inadequate, then one must intervene in an operative manner, for example with decompressive surgery. Since, as already mentioned, the stenosis patients are often older people and they often also suffer from co-morbid conditions, the risk of complications is considerable. Accordingly, one is interested in being able to perform minimal-invasive surgery which reduces the risk of complication.

In place of the very widespread stiffening of several vertebral bodies in the lumbar region, in recent years elements have been developed which may be inserted between two adjacent vertebra processes and are designed to be adjustable in height. Such implants are shown, for example, in U.S. Pat. No. 5,458,641 or U.S. Pat. No. 5,702,455. The use of these implants however requires the operator to largely open up the lumbar spinal region, in order to insert the respective element and in particular to carry out the required size adaptation. This problem has been recognized, and a corresponding solution has been suggested, which has a simplified implant which may be adapted in size in a self-regulating manner by an elastic intermediate element. The advantage of this solution is not only simpler adaptation to the bodily particularities, but also the simple construction of the element and its fixation on the vertebral processes. It would also be conceivable to apply such a solution using merely a unilateral access. However, one would not do this for safety reasons, since the element with the processes is screwed, and as a result one would operate on both sides of the spinal column for a secure control.

Further implants for dealing with lumbar spinal canal stenosis are known from EP-0,322,334 A and FR-2,724,554 A. The solution described in WO99/21501 is particularly advantageous. The implant disclosed therein operates with a central body on which a sleeve is rotatably mounted in an eccentric manner. As locking means, wings are provided on both sides of this sleeve which is oval in cross section, and these wings must bear on the central body on both sides of the vertebral processes. This size adaptation by way of the spacer which is oval in cross section, requires more space to be provided for this, and furthermore the design is set up such that the operator must have access to both sides of the vertebral column.

The main advantage of this solution is that one requires no type of screwing on the vertebral body, and the implant itself is relatively simple in its construction. There are differing opinions with regard to the requirements of an element which may be adapted in diameter to the respective situation. Certain operators are of the opinion that the size of the spacer to be inserted may be exactly defined by way of an exact diagnostic clarification and measurement. Thereby, one wishes to assume the smallest required diameter of the spacer. The smaller the implant and the smaller the operation, the lower the risk of post-operative complications.

SUMMARY OF THE INVENTION

It is therefore the object of the present invention to provide an implant for treating lumbar spinal canal stenosis which is as small and simple as possible, but which may in particular be inserted by way of unilateral intervention.

This object is achieved by an implant with a spacer which may be applied between spinous processes of two adjacent vertebrae, wherein the spacer is designed as a roller body, on which, on each of both sides, a first and a second retaining element may be brought to bear which hold the transversally running roller body bearing on the spinuous processes on both sides. The implant is designed such that it may be introduced in a unilateral manner and, in the introduced condition, the first retaining element which is distanced furthest from the introduction sides may be pivoted in position by the effect of force, so that, at the side distant to the introduction side, this comes to bear on the spinous processes.

BRIEF DESCRIPTION OF THE DRAWINGS

Preferred embodiments are shown in a simplified representation in the drawing, and are explained by way of the subsequent description.

There are shown in.

DETAILED DESCRIPTION

Figure 1:
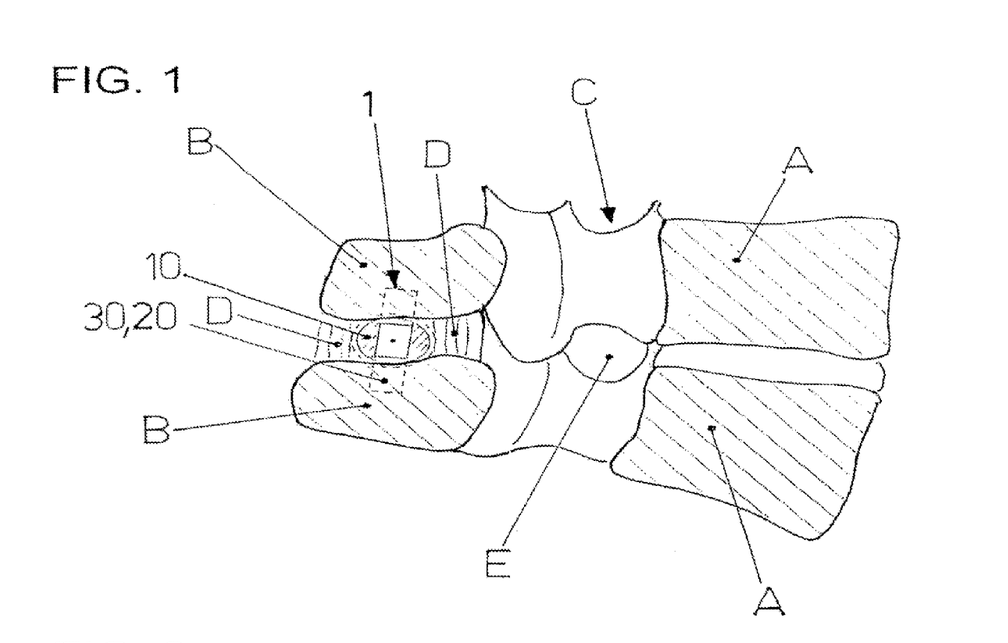
FIG. 1 the implant in its condition of installation, between two adjacent spinous processes of a vertebral body, FIG. 2 the implant according to the invention represented alone in the assembled condition, in a longitudinal section.

The situation with regard to a patient is shown in FIG. 1. Two adjacent vertebral bodies or vertebrae are shown at A. Their spinous processes are indicated at B. The spinal canal C runs between the vertebral bodies A and the spinous processes B. E represents the exit locations of the nerve roots. The interspinal ligament D runs between two adjacent spinous processes B. A spacer 10 crosses through this ligament, and in its position is secured against transversal displacement by a first retaining element 20 on the one side, and by a second retaining element 30 on the other side. This securement is however hardly effective since the spacer 10 is designed in a waisted manner and thus centers between the two spinous processes B.

Implants of this type are required when signs of the so-called Baastrup/kissing spine syndrome appear. The Baastrup syndrome indicates the contacting of two adjacent spinous processes. In this situation, the supraspinal ligament is forwardly curved towards the spinal canal and affects the spinal canal stenosis. Additionally, it may lead to an invertebral disk protrusion which further narrows the spinal canal. The spinous processes are pressed apart with the implant according to the invention, and the compressed interspinal ligament is relieved, so that the supraspinal ligament recedes and the stenosis is cured.

Figure 2:
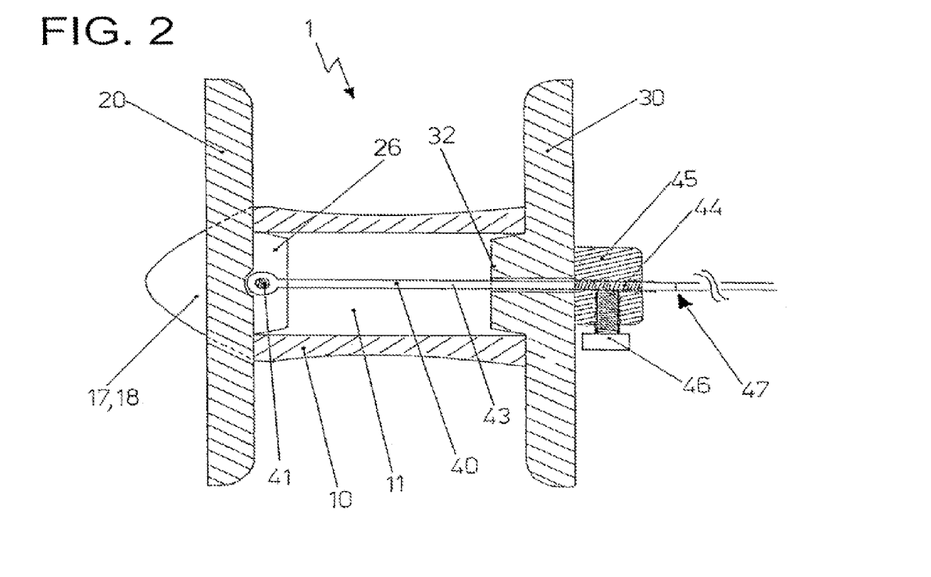
Figure 3:
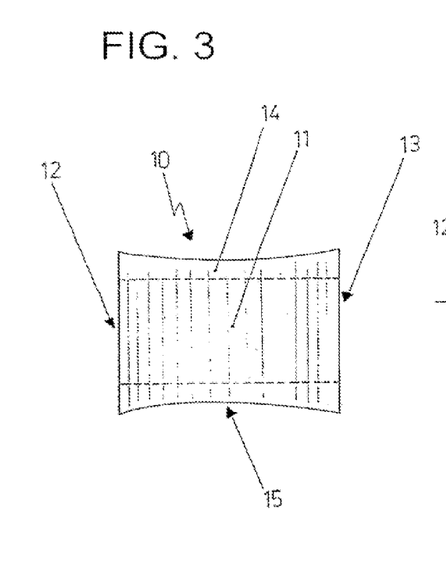
FIG. 3 shows a spacer realized as a roller body, in a lateral view.
Figure 4:
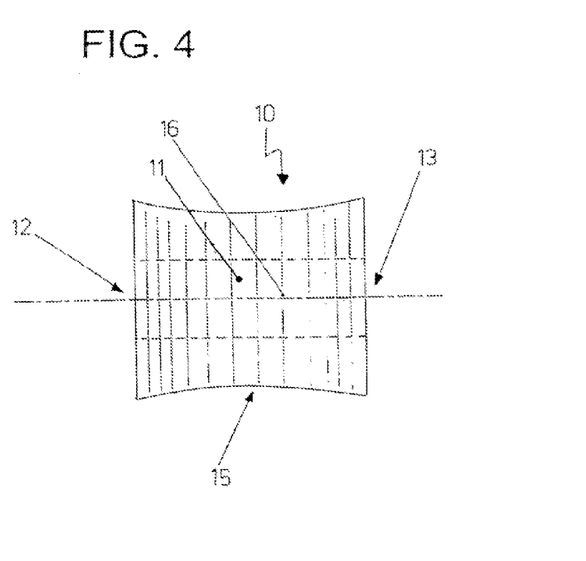
FIG. 4 the same spacer in a view from above.
Figure 5:
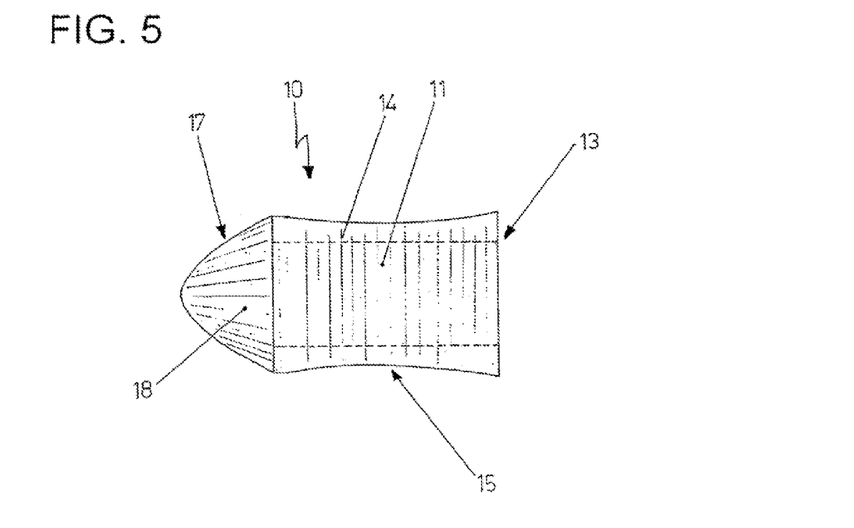
FIG. 5 shows one variant of the spacer with a pointed head, again in a lateral view, whilst
Figure 6:
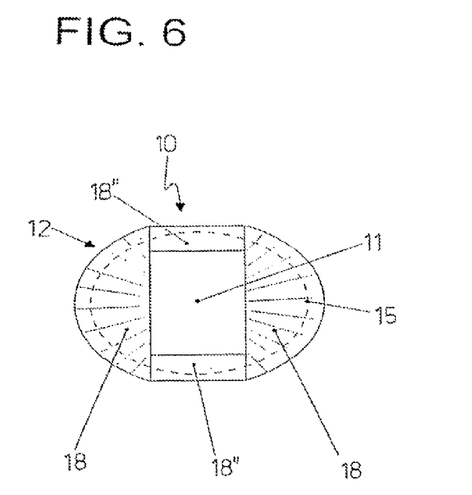
FIG. 6 shows the same spacer with a view onto the pointed end, which is the end on the introduction side
Figure 7:
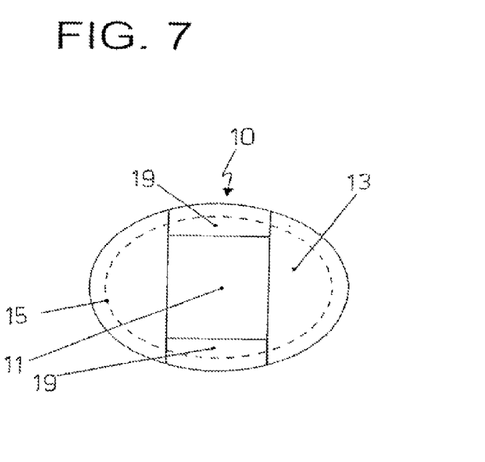
FIG. 7 shows the same spacer with a view onto the rear-side end, whilst FIG. 8 again shows the same spacer in a view from above.
Figure 8:
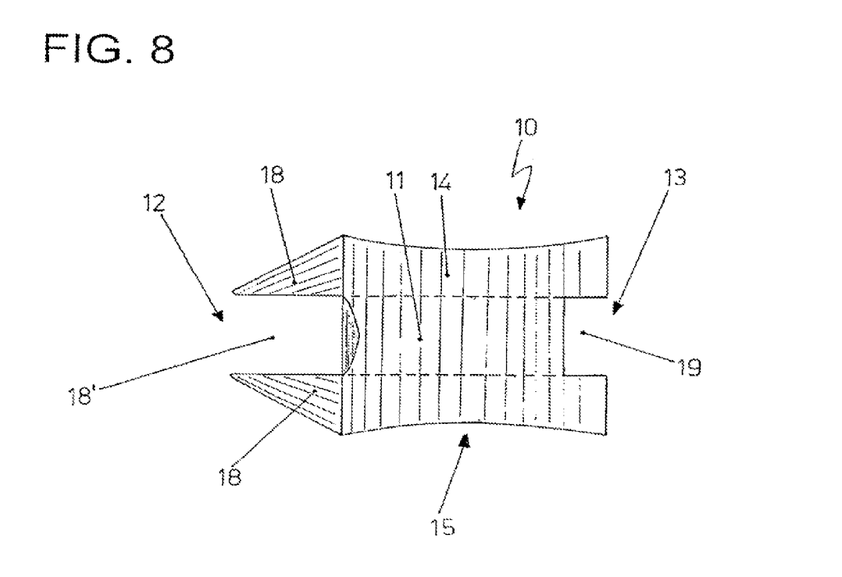

The implant according to the invention is shown in its entirety in the assembled condition in FIG. 2, and is indicated at 1. It consists of essentially four elements. The main element is a spacer 10 which is preferably designed as a roller body. This may basically be a cylindrical element. In the examples represented here, the spacer 10 is oval in cross section, whereby the spacer is seen to have two different sizes, depending on whether one represents the spacer 10 in a lateral view, as shown in FIGS. 2 and 3, or in a plan view from above, as shown in FIG. 4. The spacer 10 here has a continuous inner space 11. This may not be rotationally symmetrical, and in the example represented here, is rectangular in cross section. Accordingly, in the lateral view according to FIG. 3, the inner space is seen to be larger, and in FIG. 4 is seen to be smaller. The cross-sectional shape of the inner space 11 selected here is a shape which is preferred for reasons of manufacturing technology, but the inner space may in principle have practically any cross-sectional shape, as long as the cross-sectional shape is not round. The spacer or roller body 10 comprises a front side 12 and a rear side 13. The surface which lies at the front on the introduction side is indicated as the front side, whilst the side lying opposite the introduction side is indicated as a rear side 13. The outer peripheral surface of the spacer 10 has a waist 15. This waist should effect a self-centering between the two adjacent spinous processes when the spacer is installed.

The two end-faces 12 and 13 of the spacer 10 may be formed in a plane manner. This results in an extremely inexpensive manufacture. Most preferably however, one would provide the side 12 at the front in the introduction direction with a head, as is displayed by most embodiments which are yet to be described hereinafter, and in particular as is represented in FIGS. 5 to 8. This head 17 is divided into two parts 18. The division is effected by a transverse cut 18'. The transverse cut 18' serves for the rotationally secured positioning of a first retaining element 20 which is yet to be described and which comes to lie at least partly in this transverse cut. In order to ensure that the retaining element 20, on pulling-back towards the spacer 10, does not again get into the inner space of the spacer, the transverse cut 18' is preferably provided with rounded ramps 18".

The spacer 10 may be designed on the rear side 13 as a simple plane surface, as shown in FIGS. 3 and 4, but it is possible to also provide the rear side with a groove-like recess 19 which serves for positioning a second retaining element 30 with a positive fit and in a rotational secure manner. Of course here too, the transverse cut 18' as well as the groove-like recess 19 may have a differently designed shape when the retaining elements have been adapted accordingly.

The first or front retaining element 20 may also have different shapes. The shaping of the retaining element, in particular of the first retaining element, is determined mainly by the fact that this must be designed such that it may be led through the inner space 11 of the spacer 10. Accordingly, the first retaining element 20 is designed at least approximately the same as the cross section of the inner space 11. In the example represented here, the first retaining element 20 consists of one piece. It has essentially the shape of a flat rod and is connected to a push- and/or pull element 40 in a pivotally movable manner. The pivotally movable connection is realized by a pivot 41.

Figure 9:
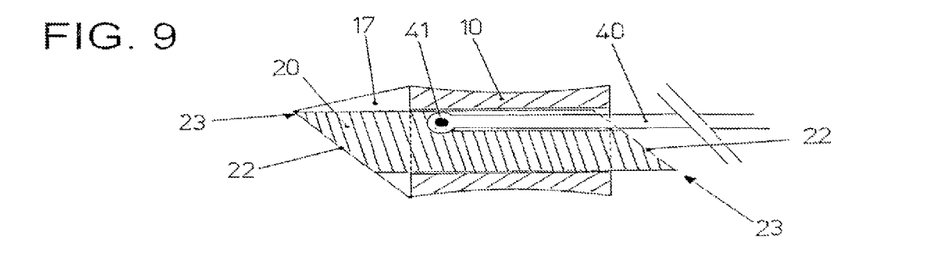
FIG. 9 shows one variant of the spacer with a first retaining element mounted thereon, in an introduction position, and FIG. 10 the same spacer according to FIG. 9 with the first retaining element in a slightly advanced position, as well as FIG. 11 the spacer and the retaining element, wherein this is located in the retaining position.

A receiver groove 21 is integrally formed roughly centrically of the longitudinal axis of the first retaining element 20. The push- and/or pull element 40 lies in the receiver groove 21 during the introduction phase, so that no projecting element exists which prevents the passage. The head 17 of the spacer 10 may, as shown in FIG. 9, be asymmetrical or, as shown in the FIGS. 10 and 11, be designed in a symmetrical manner. The first retaining element 20 comprises terminal, inclined end-faces 22. These end-faces 22 run into cutting edges 23. With the pushing of the first retaining element 20 through the inner space 11, the inclined end-faces with their cutting edges 23 sever the interspinal ligament. Thereby, a torque is simultaneously created by the inclined end-faces 22, whereby the first retaining element 20 tends to come into a certain pivot movement. This pivot movement only occurs when the first retaining element 20 is completely led through the spacer 10. Thereafter, a pulling movement is applied onto the push- and/or pull element 40, the first retaining element changes sides and comes to lie with its wide longitudinal surface onto the part surface, here shaped in a plane manner, in the transverse cut 18" between the two parts 18'. As will be shown later, the actual spacer is previously introduced by way of a special forceps, and thereby simultaneously pushed through the interspinal ligament. The cutter 23 only simplifies the introduction when a certain back-deformation is affected by the elasticity.

Figure 10:
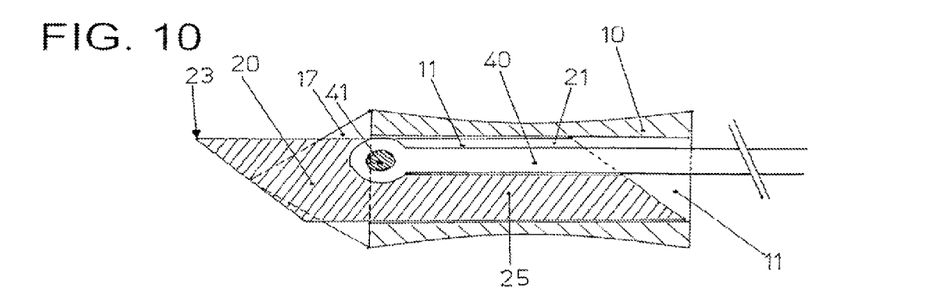
Figure 11:
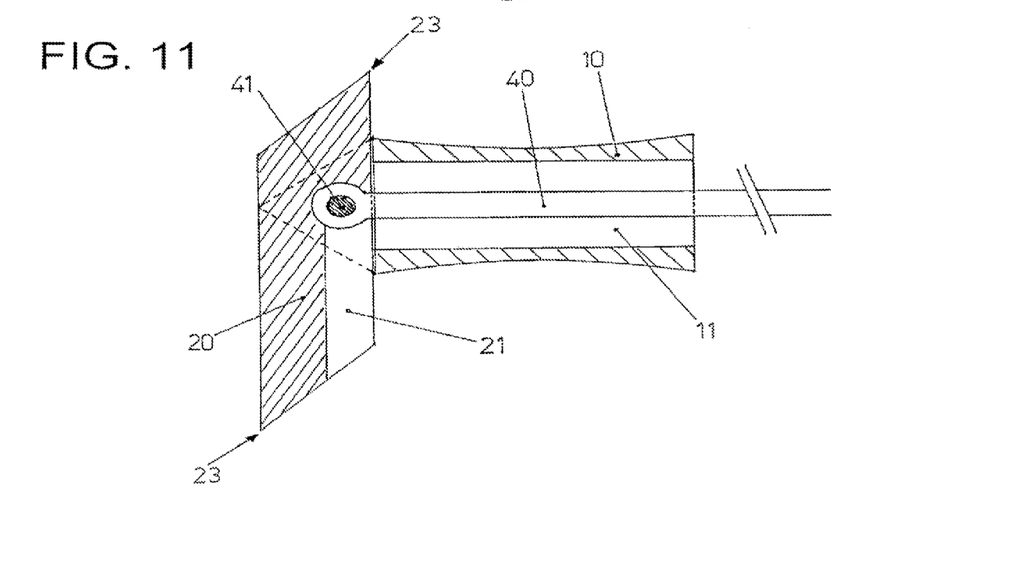
Figure 12:
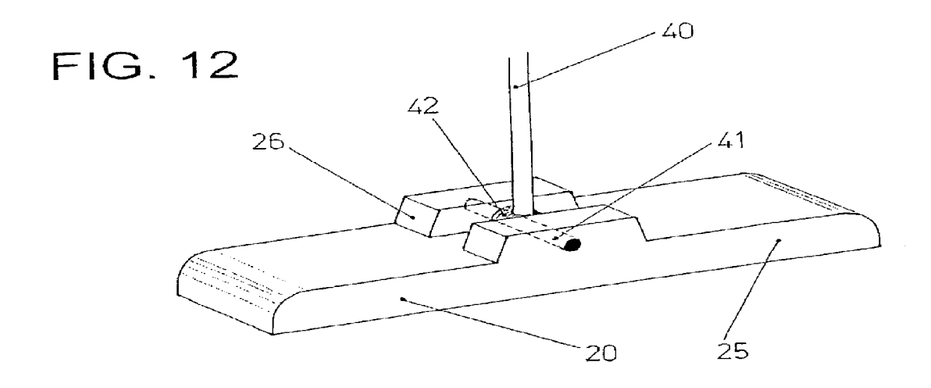
FIG. 12 shows a first retaining element in a single-piece design in a perspective representation, with a push- and/or pull element connected thereto in a hinged manner.
Figure 13:
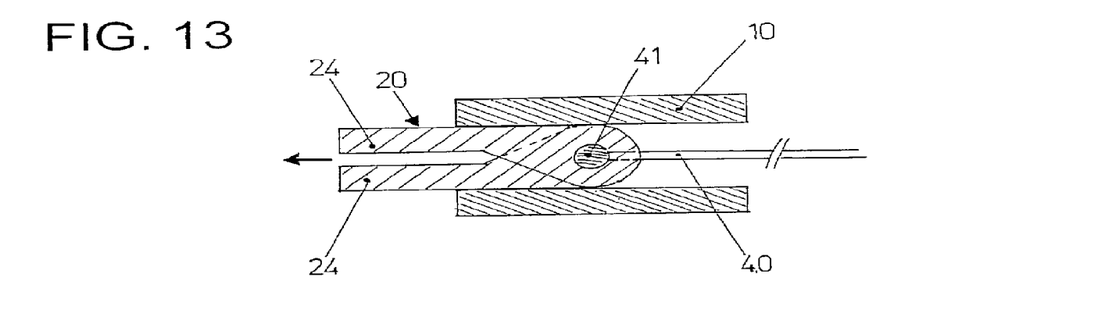
FIG. 13 again in a simplified manner, shows a spacer with a partly led-through, first retaining element, wherein here it is the case of a two-part retaining element
Figure 14:
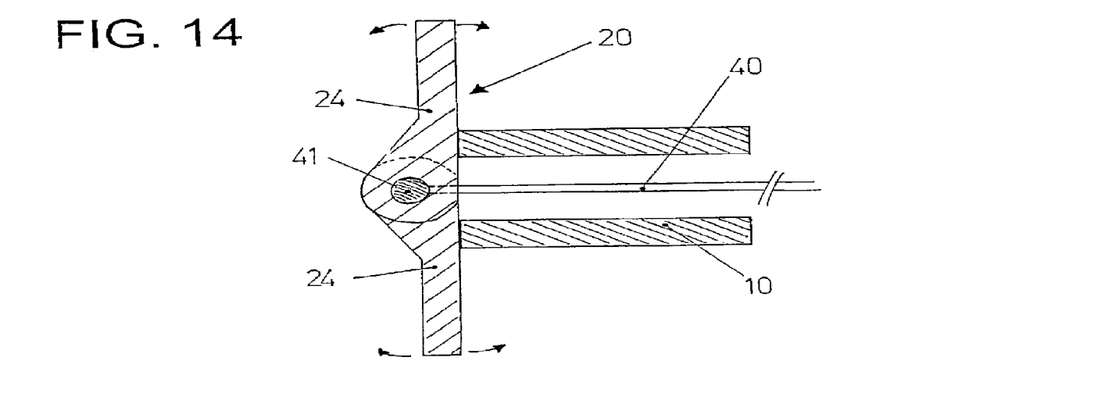
FIG. 14 shows the same element according to FIG. 13 in the retaining position.

Apart from the preferred embodiment according to the FIGS. 9 to 11 shown here, it is also possible to realize the retaining element 20 in a different shape, as shown in FIG. 12. Here too, a single-piece, first retaining element 20 is employed. This too has roughly a rod-like shape. The cross-section of this first retaining element is however smaller than the cross section of the inner space 11. It only reaches the full cross section in the middle region, where the rod-like part 25 is provided with a plateau 26. The plateau 26 here serves for mounting the already mentioned pivot pin 41. The push- and/or pull element 40 in turn is integrally formed on this pivot pin 41. In this embodiment, a torsion spring 42 is also attached on the pivot pin 41, and rotates the rod-like part 25 of the retaining element 20 relative to the push- and/or pull elements after completely pushing through the inner space 11 of the spacer 10, so that the first retaining element 20 is not pulled into the inner space again on retraction.

FIGS. 13 to 16 show two variants of a first retaining element 20 which is designed of two parts. Here, the rod-like part 25 is divided into two part rods 24. In the embodiments according to FIGS. 13 and 14, the first retaining element is designed such that the two part rods 24 may be inserted with their freely movable ends at the front. The two part rods are held in a pivotally movable manner on the same pin 41 on which the push- and/or pull element 40 also engages. With this embodiment, the two part rods 24 must be spread apart by way of a relatively strong spring, which then permits a retraction only under relatively large tensile forces. The great advantage of such a solution lies in the fact that the unilateral installation is reversible, and as a result, if necessary, the complete implant may be unilaterally removed in a subsequent operation.

Figure 15:
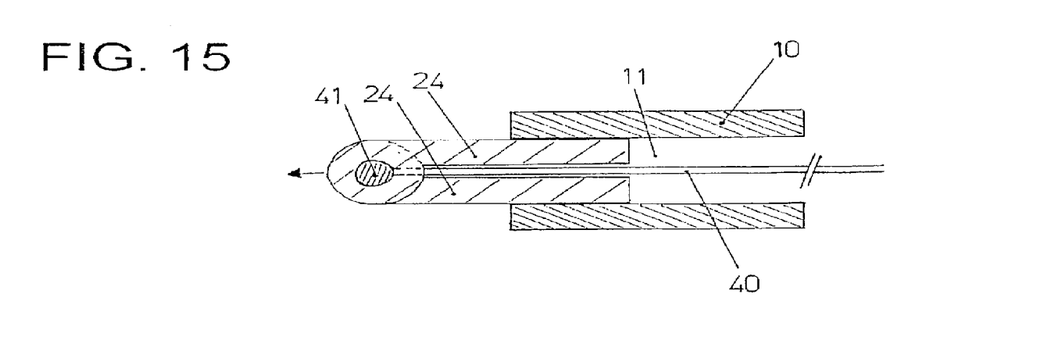
FIG. 15 shows an alternative first retaining element, again in a partly led-through condition, in a longitudinal section, whilst
Figure 16:
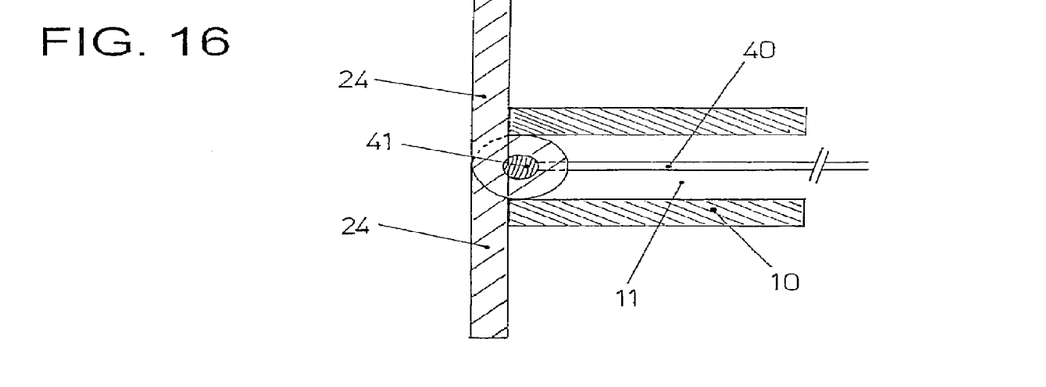
FIG. 16 shows the same two-part element according to FIG. 15 in the retaining position.
Figure 17:
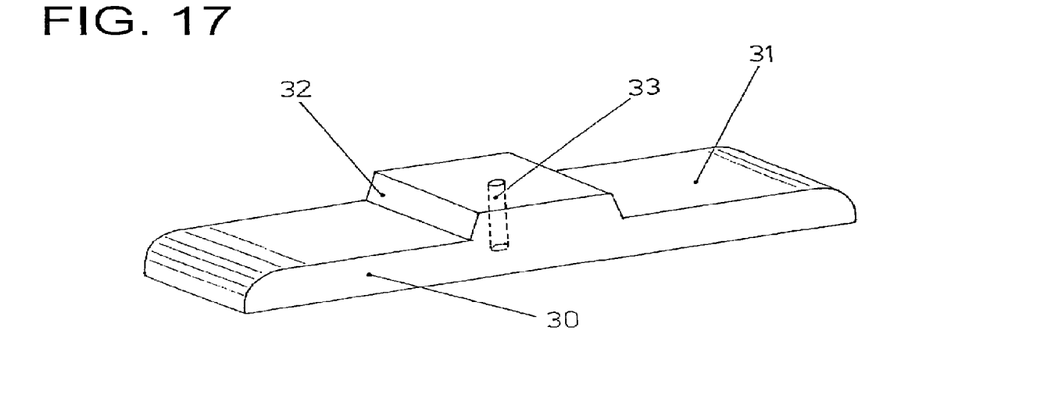
FIG. 17 shows a second retaining element in a simplest design, in a perspective view and FIG. 18 a part of the spacer with a second retaining element which may be attached thereon, in a lateral view.

With the embodiment according to the FIGS. 15 and 16 unilateral removal is no longer practical. Otherwise however, the first retaining element 20 is designed in a very similar manner. Whereas with the embodiment according to FIGS. 13 and 14, the pivot axis 41 follows the two part rods 24 in the push-through/piercing direction, here the hinge is displaced to the front, and thus lies at the front in the push-through direction. Otherwise, the element has the same parts and these are provided with the same reference numerals. The spacer 10, although this is not represented here, may of course be provided with a somewhat rounded run-out stretch at the front side, so that a certain spreading may already be effected during the pushing-through of the folded-together, two-part retaining element 20 in the final phase of the pushing-through. The second retaining element 30 is usefully always designed as one piece. This too has a somewhat rod-like shape. The design of this second retaining element may be particularly simple since this is attached on the side which is freely accessible during the operation. In the present case, it consists of the rod-like body 31 with a plateau attachment 32.

The plateau attachment 32 is designed with regard to shape such that it may be attached with a positive-fit from the rearward side, wherein the plateau 32 is accommodated in the inner space 11 of the spacer 10 with a positive fit and secured against rotation.

A central bore 33 passes through the rod-like part 31 and the plateau 32, and the push- and/or pull element 40 may be led through this bore. This situation may be clearly seen in FIG. 2. As FIG. 2 clearly shows, the plateau 26 on the first retaining element 20 may also be designed such that it engages in the inner space 11 of the spacer with a positive fit and in a rotationally secure manner. The push- and/or pull element 40 as mentioned, passes through the second retaining element 30 with its rod-like part 43 and projects outwards on the rearward side. The rod-like part 43 comprises a thread 44 at the rearward end. A retaining nut 45 is screwed onto this thread 44. A threaded bore which passes through the retaining nut 43 up to the center serves for the insertion of a securing screw 46. When the nut 45 is secured by way of the screw 46, thereafter one would then cut away the rod-like part 43 of the push- and/or pull element 40 as close as possible to the nut 45. The arrow 47 indicates this separation.

Figure 18:
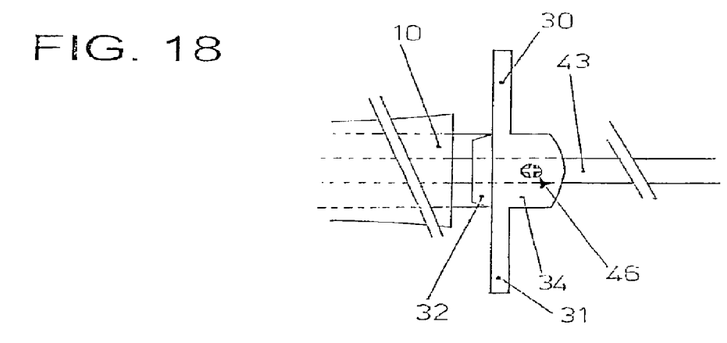

A variant of the second or rear-side retaining element 30 is represented in FIG. 18. This again has a rod-like body 31 and likewise a plateau attachment 32 which is accommodated in the inner space of the spacer 10. With this solution, a guide head 34 is additionally integrally formed on the rearward side opposite the plateau attachment. This guide head may guide the rod-like part 43 of the push- and/or pull element 40. The through-bore 33 in this case may also be designed as a threaded bore. This however is not absolutely necessary. Since in this embodiment greater guidance for the securing screw 46 is provided, the securing screw 46 may be designed as a grub screw which is provided with a tip which penetrates into the rod-like part 43 with a positive fit. Thereby, in practice, a cold-welding may occur. An extremely secure connection may thus be realized.

Figure 19:
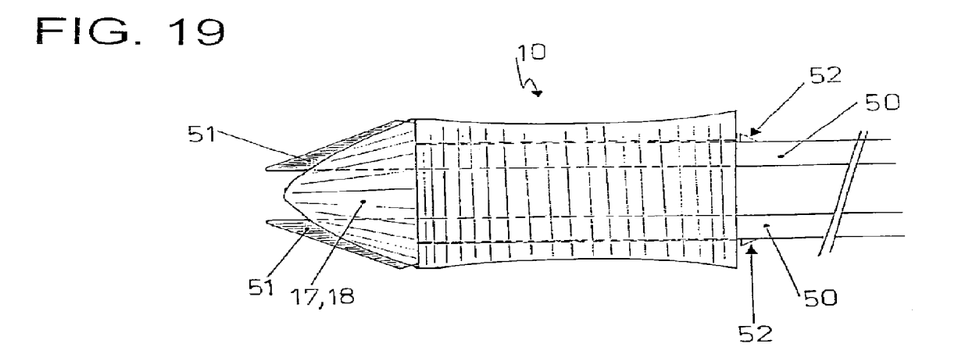
FIG. 19 symbolically and in a simplified manner, shows a spacer with two introduced clamping jaws of a forceps, which serve for introducing the spacer, in the lateral view, and FIG. 20 the same situation in a view from the front.
Figure 20:
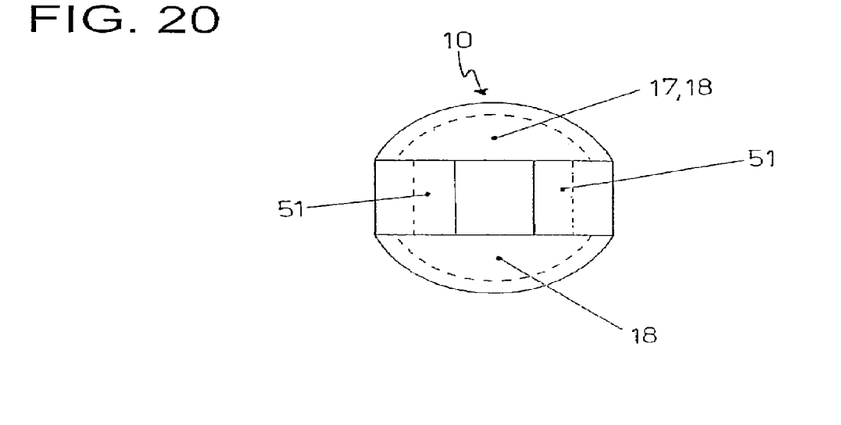

The invention likewise includes a forceps preferred for placing the implant. FIG. 19 illustrates the jaws 50 of the forceps. The forceps jaws 50 are designed such that, when lying completely on one another, they may be guided through the inner space 11 of the spacer 10. The jaws 50 also have jaw tips 51. These jaw tips 51 supplement the head 17 of the spacer when the forceps jaws are introduced, and are spread apart.

Once the spacer has been placed on the forceps jaws, one then guides the spacer with the forceps from one side between and through two adjacent spinous processes, and thereby penetrates the intraspinal ligament. For simplifying the leading-through, the operator creates the guide-through opening by way of a scalpel, at least in a slot-like manner. Retaining beads 52 are furthermore formed on the jaws 50, to prevent slipping of the spacer on the jaws 50. The forceps jaws 50 however also hold the spacer 10 with a non-positive fit and thereby bear on the inner surface of the inner space 11 with their outer surfaces.

Figure 21:
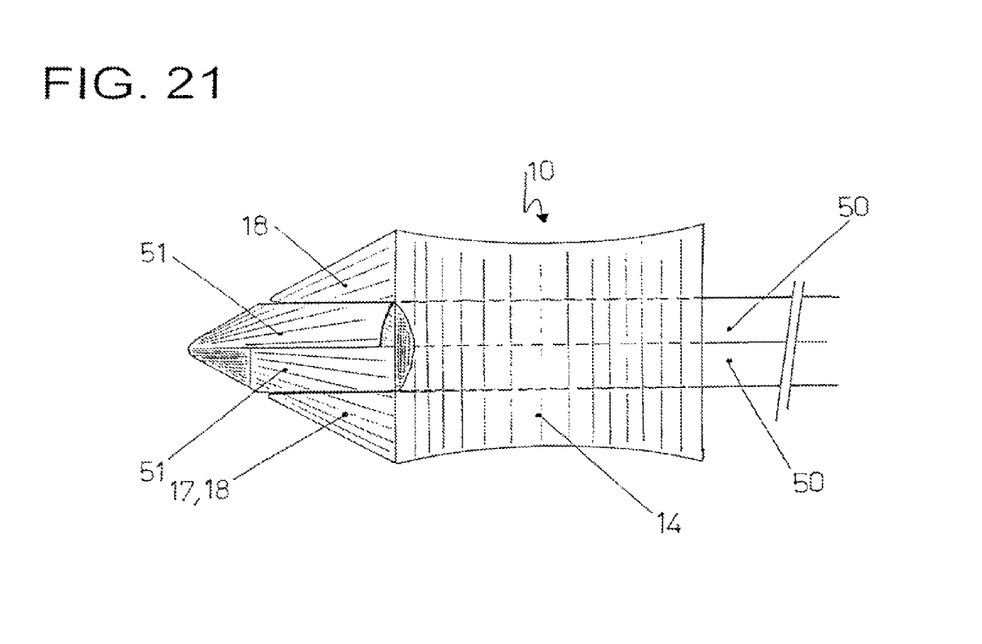
FIG. 21 shows a similar spacer with a differently shaped introduction forceps, whose jaws are designed running past one another in a shearing manner. Finally
Figure 22:
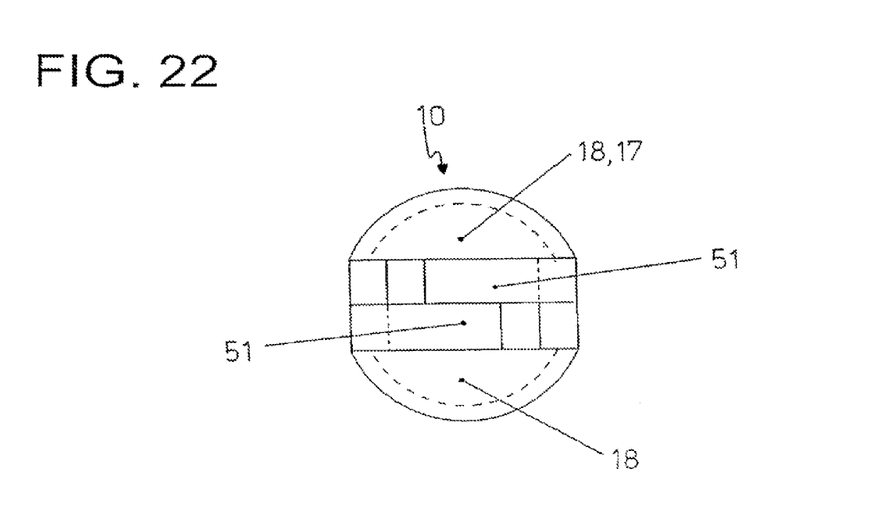
FIG. 22 shows the situation of FIG. 21 in a view of the tip of the clamping jaws of the forceps, or of the introduction side of the spacer.

One possible variant of the forceps is represented in FIGS. 21 and 22. Here, the two jaws of the forceps slide over one another in the manner of a scissors. The two jaws 50 again have jaw tips 51 which complement the head 17 of the spacer 10 into a tip. The jaw tips 51 thereby may be perfectly adapted to the head shape. This permits a shape which is more closed in the penetration direction, than with the previously mentioned embodiment of the forceps. Although the forceps represents a preferred embodiment for application of the implant, it is of course also possible to realize differently shaped introduction means. The embodiment described here merely serves for disclosure of the complete implementation of the invention, thanks to which it is possible to only carry out an opening of two adjacent spinous processes in the region of the lumbar vertebral channel stenosis from only one side, whereupon the implant may be placed thanks to the unilateral manner of installation.

Figure 23:
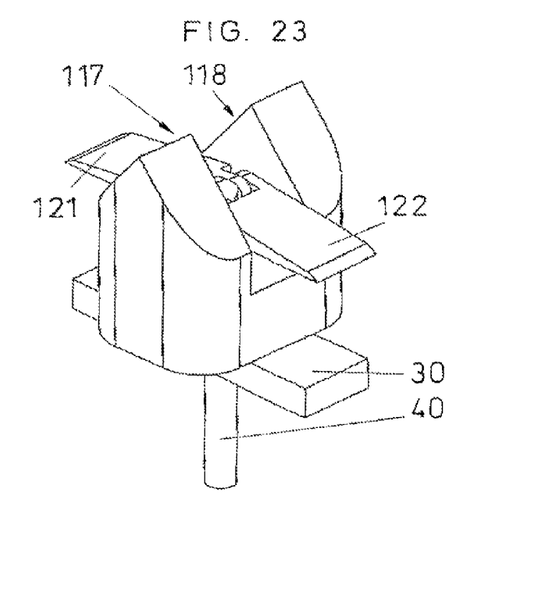
FIG. 23 shows an embodiment which is designed in a detailed manner, according to the variant according to the FIGS. 15 to 17, in a perspective representation in the introduction position, as well as FIG. 24 in the lateral view.
Figure 24:
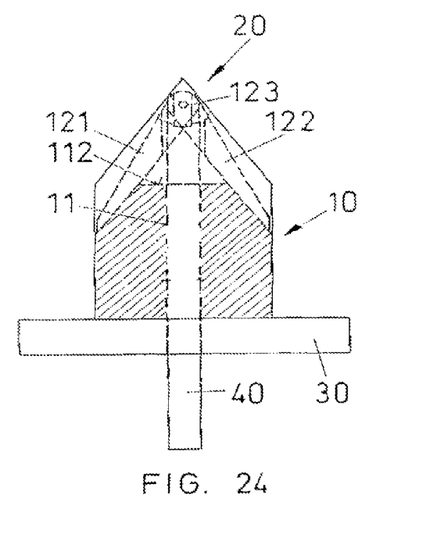
Figure 25:
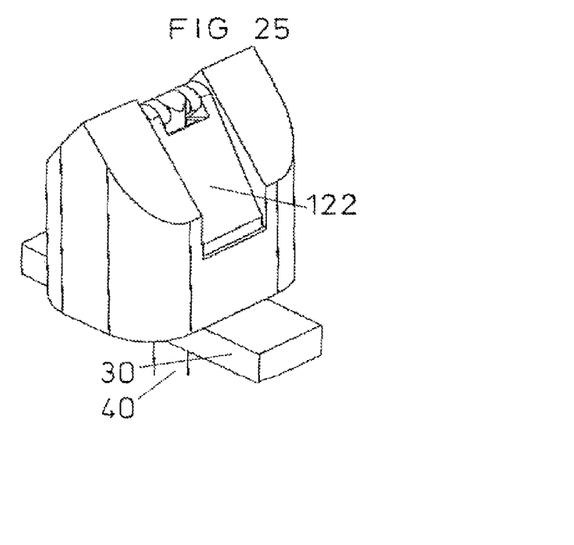
FIG. 25 shows the embodiment according to FIG. 23 in the introduced end position, again in a perspective representation and FIG. 26 in a lateral view. Finally, a solution which is particularly preferably with regard to handling is shown in FIG. 27 in the introduction position, in a perspective representation.
Figure 26:
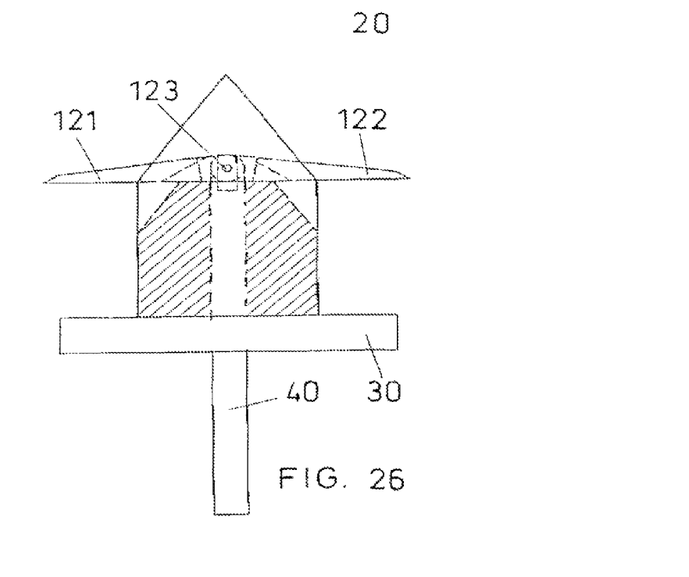

A version which is modified with respect to the previously described embodiments is represented in FIGS. 23 to 26, wherein this implant for treating lumbar spinal canal stenosis achieves the same object of the invention, specifically of providing an implant which may be applied by way of a unilateral intervention. However, whereas with all previous embodiments, the first retaining element 20 was led through the spacer 10, here a solution is shown, with in which the first, front retaining element 20, is designed of two parts. The two parts of the retaining element 20 are here indicated with the reference numerals 121 and 122. The surface which lies at the front during the introduction of the spacer 10 between the two spinous processes B is represented here as a head 117. The head 117 here has a roof-like design. The head 117 has a crossing incision 118. This incision 118 likewise has a roof-like shape, whose tip however is ground-off. Accordingly, a plane part surface 112 remains. The two parts 121 and 122 of the first, two-part retaining element 20 are held on the tensile- or compressive element 40 in a pivotally movable manner via a pivot 123. The pivot 123 passes through the pull and/or push element 40, and the two parts 121 and 122 engage around the tensile- or compressive element 40 designed as a rod. Since in this case, the first retaining element 20 thus no longer needs to be guided through the spacer 10, it is also not necessary for the inner space 11 to have a design which differs from the round shape. The rotational securement results from the positive-fit mounting of the two-part first retaining element, which lies integrally in the head 117 of the spacer 10 already on applying the implant, thus in the introduction position. After the implant has been correctly placed between the two adjacent spinous processes, it is then sufficient to pull on the push- and/or pull element 40, by which means the two parts 121 and 122 automatically come out of the position as shown in FIG. 23, into the end position as shown in FIG. 25. In this position, the two parts 121 and 122 then lie on the plane part surface 112 and now remain in this position. Thereafter, as a locking element, one then slides the second rearward retaining element 30 over the push- and/or pull element, until the second retaining element 30 bears on the spacer 10. Thereby, it is not at all the case that the first retaining element and the second retaining element bear laterally on the spinous processes, but these processes serve merely as a securement in order to prevent a displacement out of this position. If the two elements were to bear flush on the spinous processes, then this would in practice be equal to a partial stiffening of the backbone, and this is not necessary in most cases of lumbar spinal canal stenosis.

Although the push- and/or pull element 40 in the embodiment represented here is realized as a round rod, for example as a threaded rod, this is not absolutely necessary. The push- and/or pull element may indeed, as previously mentioned, have a non-round shape and accordingly the inner space 11 would in turn have a non-round shape. The embodiment represented here is relatively simple in handling and design. The spacer 10 may be introduced in the position as is shown in the FIGS. 23 and 24, whilst simultaneously the second, rearward retaining element 30 is held secured on the push- and/or pull element 40 such that the relative positions are as shown in the FIGS. 23 and 24. Accordingly, the implants may be supplied in this preassembled condition. On introduction, pressure may be applied directly onto the push- and/or pull element 40. Once the end position is reached, one may then exert tension on the push- and/or pull element, while compression is simultaneously exerted on the second retaining element 30. This causes elements 30 and 40 to displace relative to one another, and only the securing part, for example a locking nut then needs to be rescrewed to the new position.

Whilst, in the embodiment shown here, the spacer 10 essentially has the shape of an octagon rounded at the corners, this is of course not absolutely necessary. Here too, the spacer 10 may in principle have the shape of a roller body. Likewise, as in the previously described examples, the spacer 10 may have a waist in order to exert a self-centering effect. In principle, a roller body is to be understood as a spacer which is axially symmetrical, but not rotational symmetrical. The term roller body merely expresses the fact that the spacer in its condition of use also serves for the spinous processes to be able to roll along thereon given movement.

Figure 27:
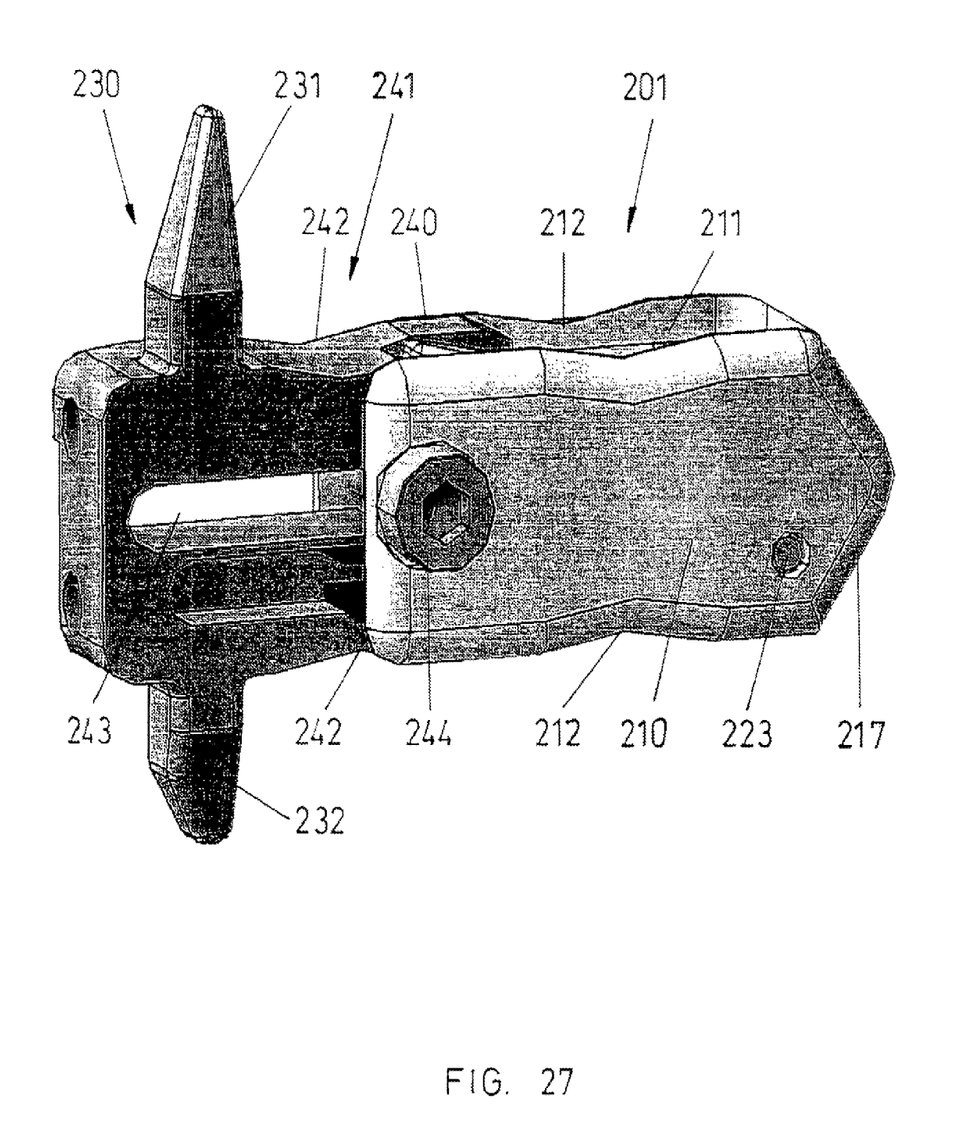
Figure 28:
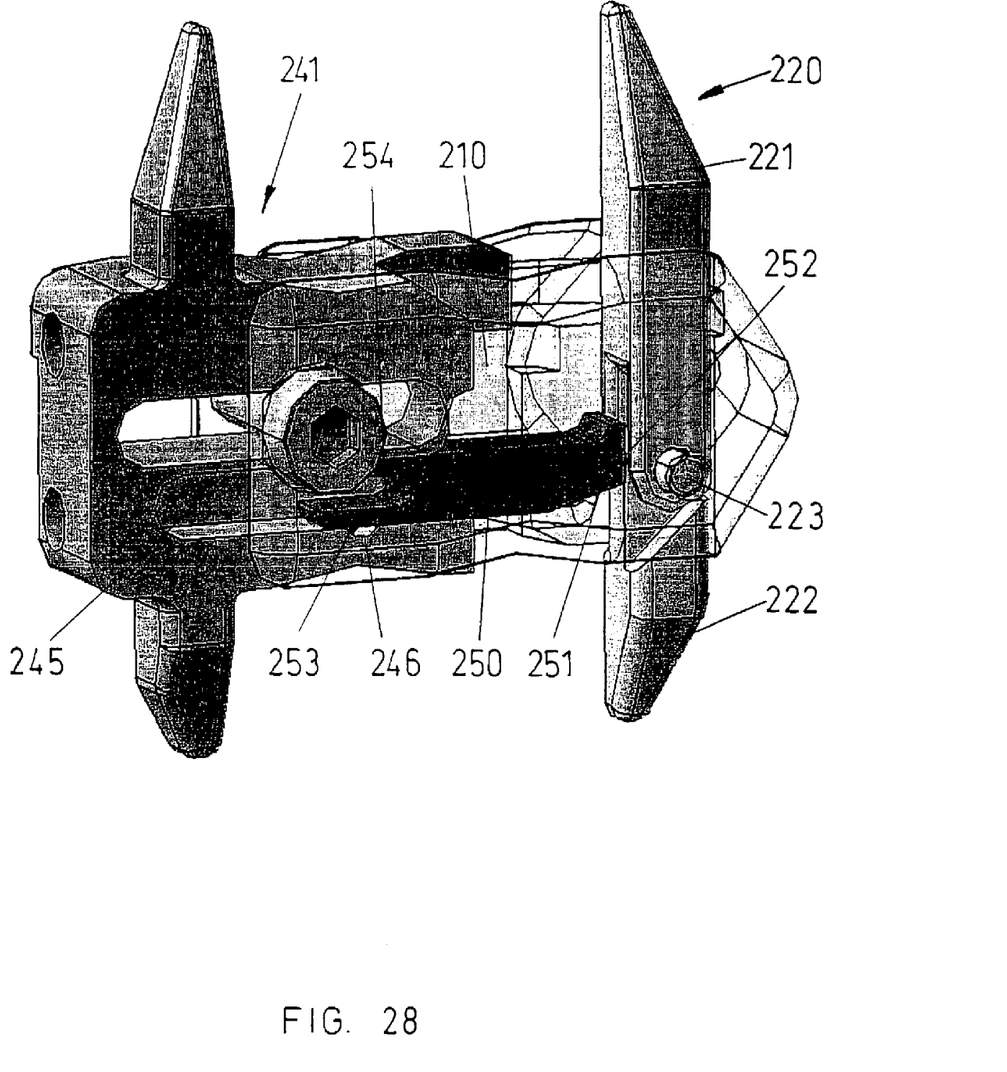
FIG. 28 shows the same solution as in FIG. 27, but in an intermediate position during the attachment, wherein the implant is shown in a phantom view. And finally
Figure 29:
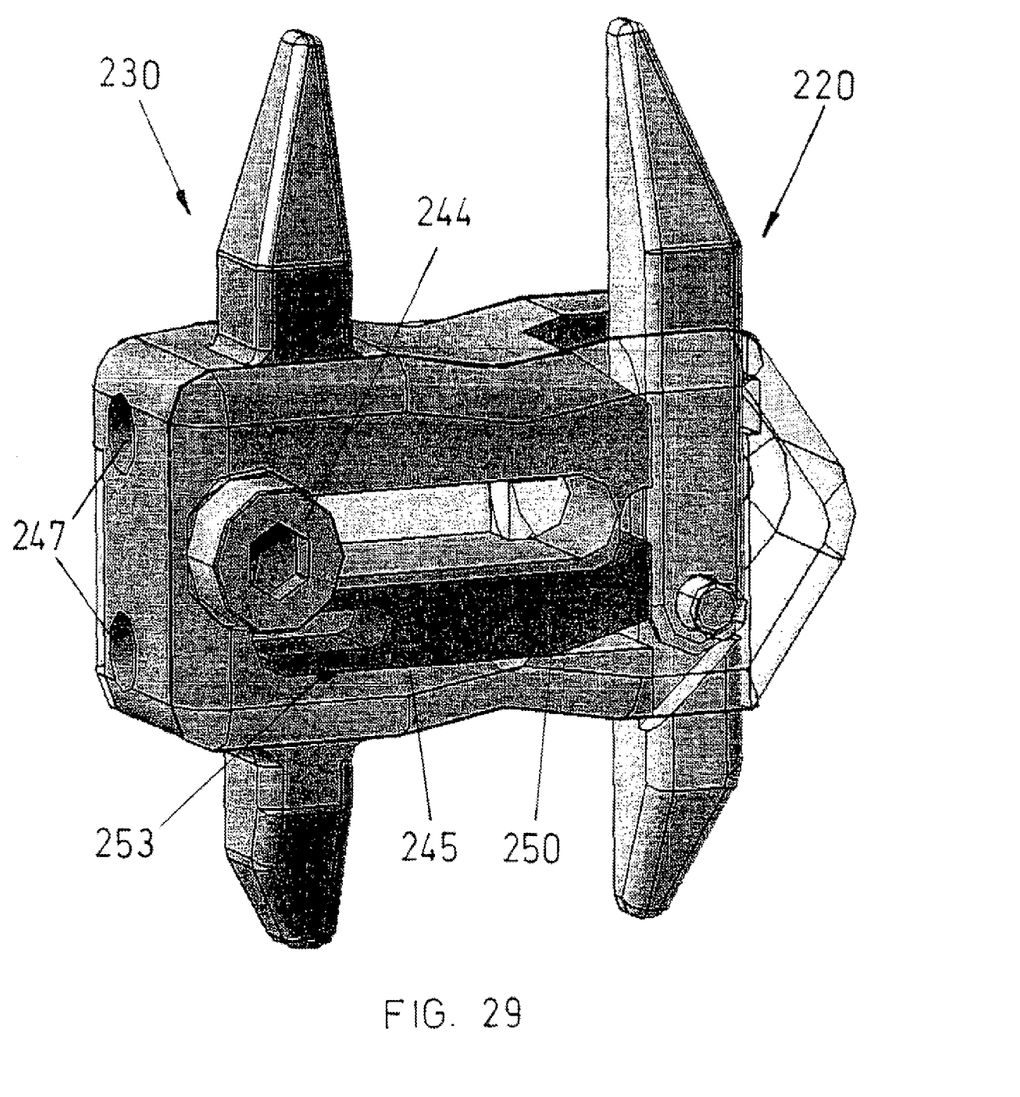
FIG. 29 shows the solution in the installed position.

The preferred embodiment represented in FIGS. 27 to 29 utilizes the idea of designing the complete implant, which here is indicated at 201, such that in an introduction position, the implant 201 in the longitudinal direction is larger than in the installed condition. By way of this, one creates additional space, in order during the introduction phase to accommodate the first, front retaining element 220 in the spacer 210 in a simpler manner, by which means this may also be designed in a more optimal manner. The spacer 210 now comprises an inner space 211 which has a longitudinal slot which extends over the whole length of the roller body 210 with the exception of the end region which forms the head 217. Now the first, front retaining element 220 may be arranged in this free space which represents the inner space 211, without any problem. The first, front retaining element 220 again is divided into two here, and the two parts 221 and 222 of the first retaining element 220 are held in a pivotable manner about a pivot 223. Thereby, the pivot 223 is attached from the middle of the spacer 210, so that the first, front retaining element is divided into a long retaining element part 221 and a short retaining element part 222.

Furthermore, the implant 201 comprises a push- and/or pull element which is indicated here at 240. This push- and/or pull element comprises an insert part 241. Connected as one piece to this is the second, rearward retaining element 230 which consists of an upper retaining element part 231 and of a lower retaining element part 232. Both parts are integrally formed on the insert part 241 as one piece. They are diametrically opposite one another. The insert part 241 is held in an extended position in the introduction phase of the implant 201, as is represented in FIG. 27. The insert part 241 at the bottom and top in each case has a saddle-like waist 242 which in shape corresponds to a same type of waist 212 on the spacer 210. In the extended condition, these two waists are separated from one another by the push-out distance. A central elongate hole 243 is integrally formed in the insert part 241. The shank of a crossing clamping screw 244 projects through this elongate hole 243. The clamping screw 244 serves for the securing of the insert part 241 in a desired retraction or extension position of the insert part 241 in the spacer 210. The spacer 210 in the end region where the clamping screw 244 is arranged, may be pressed together slightly, thanks to the inner space 211 being designed as an elongate slot. During the introduction phase, the insert part 241 is clamped in the extended position by way of the screw 244.

A longitudinal groove 245 is formed below the elongate hole 243 parallel to this. A plunger 250 is mounted in this longitudinal groove 245. The plunger 250 has a lug 251 and a press surface 252. By way of the lug 251, the plunger, on collision of the insert part 241 into the spacer 210 which here are represented in a transparent manner, pushes the two retaining element parts 221 and 222 apart, whilst in the end position, the front press surface 252 lies in a flat manner on both retaining element parts 221 and 222 engaging into one another in the hinge region. The longitudinal groove 245 has a locking flute 246 which is arranged in the front region, whilst the plunger 250 comprises a bead 253 which in the position according to FIGS. 27 and 28 (i.e. in the introduction position) and in the intermediate position of the pushing together, is mounted in locking flute 246. The plunger 250 furthermore at the end has a longitudinal slot 254 which extends beyond the region on which the bead 253 is attached. By way of this, the end region of the plunger 250 may be pressed together in a resilient manner, so that the bead 253 may be pressed out of the locking flute 246 when the insert part 241 is pushed into the spacer 210. This inserted condition which corresponds to the installation position of the implant, is represented in FIG. 29. In this position, the plunger 250 is completely inserted in the longitudinal groove 245. This is evident in FIG. 29 because here too the spacer 210 is represented in a transparent manner. The bead 253 now lies in a rear position, at which a locking flute may be present. However, the flocking flute is not absolutely necessary, and is not shown in the other Figures.

The solution shown in FIGS. 27 to 29 for a post-operative intervention may also be unilaterally disassembled again. For this, the locking screw 244 fixed in the end position is released again, and thereafter is introduced through two insert bores 247 incorporated from the end side, by way of a tool which comprises two parallel round rods connected to one another. Whilst pressing on the tool, one simultaneously pulls the insert part 241 by way of tension on the rearward, second retaining element 230 which now lies free, so that, while the insert part 241 is being pulled out, the plunger 250 remains in its rearward position whilst pressure by the tool through the upper bore 247 onto the upper part of the two-part first retaining element part 221, permits the two parts 221 and 222 to be folded back, so that finally again the position according to FIG. 27 is reached. In this position, one may of course remove the complete implant without any problem.

LIST OF REFERENCE NUMERALS

A vertebrae
B spinous processes
C spinal canal
D interspinal ligament
1 implant, entirety
10 spacer, roller body
11 inner space
12 surface on the introduction side, plane, front side
13 rear side
14 wall
15 waisting
16 longitudinal axis of the roller body
17 head of the spacer
18 part crest
18' crossing incision
18" ramps
19 groove-like groove
20 first, front retaining element
21 receiver groove
22 inclined end surface
23 cutting edges
24 part rods
25 rod-like part
26 plateau
30 second, rearward retaining element
31 rod-like body
32 plateau attachment
33 through bore
34 guide head
40 push- and/or pull element
41 pivot
42 torsion spring
43 rod-like part
44 thread
45 retaining nut
46 securing screw
47 separation
50 forceps jaws
51 jaw tips
112 plane part surface
117 head
118 crossing incision
121 part of retaining element 20
122 part of retaining element 20
123 pivot
201 implant
210 spacer
211 inner space
212 waisting
217 head
220 first, front retaining element
221 long retaining element part
222 short retaining element part
223 pivot
230 second, rearward retaining element
231 upper retaining element part
232 lower retaining element part
240 push- and/or pull element
241 insert part
242 saddle-like waisting
243 elongate hole
244 clamping screw
245 longitudinal groove
246 locking flute
247 insert bore
250 plunger
251 lug
252 press surface
253 bead
254 longitudinal slot

The invention claimed is:

1. An implant for treating lumbar spinal canal stenosis comprising:
   (a) a spacer which can be applied between spinous processes of two adjacent vertebrae, the spacer comprising a front, introduction, side and a rear side and an inner space extending longitudinally through the spacer between the front side and the rear side, wherein the spacer is partly slotted in a longitudinal manner to form a longitudinal slot and wherein the front side of the spacer comprises a formation which extends from the front side of the spacer and forms a part crest or roof;
   (b) a first retaining element consisting of a first part and a second part which are pivotally held with one another via a pivot, wherein the first retaining element is positioned in the longitudinal slot during introduction of the spacer and can be brought to bear on the spinous processes in proximity to the front side of the spacer after introduction of the spacer;

(c) a second retaining element that can be brought to bear on the spinous processes in proximity to the rear side of the spacer after introduction of the spacer; and (d) a push-pull element comprising an insert part, the insert part being displaceably mounted in the longitudinal slot, wherein the insert part comprises a plunger which, on insertion into the longitudinal slot, presses on the first part and the second part of the first retaining element and presses the first part and the second part of the retaining element apart, wherein the spacer comprises a waisted peripheral surface whereby a self-centering of the spacer between two spinous processes is effected.

2. An implant according to claim 1, wherein a rotationally secured positive-fit connection exists between each of the first and second retaining elements when the first and second retaining elements are in the retaining position.

3. An implant according to claim 1, wherein the longitudinal slot of the spacer has a rectangular or square cross-sectional surface.

4. An implant according to claim 1, wherein the second retaining element comprises a plateau, which, in a retaining position, engages into the inner space of the spacer with a positive fit and in a rotationally secure manner.

5. An implant according to claim 1, wherein the second retaining element is provided on the insert part.

6. An implant for treating lumbar spinal canal stenosis comprising:

(a) a spacer which can be applied between spinous processes of two adjacent vertebrae, the spacer comprising a front, introduction, side and a rear side and an inner space extending longitudinally through the spacer between the front side and the rear side, wherein the spacer is partly slotted in a longitudinal manner to provide a longitudinal slot;

(b) a first retaining element consisting of a first part and a second part which are pivotally held with one another via a pivot, wherein the first retaining element is portioned in the longitudinal slot during introduction of the spacer and can be brought to bear on the spinous processes in proximity to the front side of the spacer after introduction of the spacer;

(c) a second retaining element that can be brought to bear on the spinous processes in proximity to the rear side of the spacer after introduction of the spacer; and (d) a push-pull element comprising an insert part that is displaceably mounted in the longitudinal slot, wherein the insert part comprises a plunger which, on inserting into the longitudinal slot, presses on the first part and the second part of the first retaining element and presses the first part and the second apart, wherein the spacer comprises a waisted peripheral surface whereby a self-centering of the spacer between two spinous processes is effected.

7. An implant according to claim 6, wherein a rotationally secured positive-fit connection exists between each of the first and second retaining elements when the first and second retaining elements are in a retaining position.

8. An implant according to claim 6, wherein the longitudinal slot of the spacer has a rectangular or square cross-sectional surface.

9. An implant according to claim 6, wherein the second retaining element is provided on the insert part.

10. An implant according to claim 6, wherein the front side of the spacer comprises a formation which extends from the front side of the spacer and forms a part crest.

* * * * *